United States Patent [19]

Kopp et al.

[11] 4,108,165
[45] Aug. 22, 1978

[54] TRANSDUCER PROBE FOR PULSE-ECHO ULTRASONIC EXPLORATION

[75] Inventors: Edward L. Kopp, Centre Hall; Paul A. Meyer; James N. Sabol, both of Lewistown, all of Pa.

[73] Assignee: Krautkramer-Branson, Incorporated, Stratford, Conn.

[21] Appl. No.: 808,066

[22] Filed: Jun. 20, 1977

[51] Int. Cl.² .............................................. A61B 5/10
[52] U.S. Cl. ................................ 128/2 V; 128/24 A; 128/221
[58] Field of Search ................... 128/215, 218 N, 220, 128/221, 24 A, 92 EB, 2 V, 2.05 Z

[56] References Cited

U.S. PATENT DOCUMENTS

| | | | |
|---|---|---|---|
| 1,596,004 | 8/1926 | Bengoa | 128/221 |
| 2,479,645 | 8/1949 | Silverstein | 128/215 |
| 3,545,443 | 12/1970 | Ansari | 128/347 |
| 3,556,079 | 1/1971 | Omizo | 128/24 A X |
| 3,677,244 | 7/1972 | Hassinger | 128/221 |
| 3,721,227 | 8/1971 | Larson et al. | 128/2 V |
| 4,037,592 | 7/1977 | Kronner | 128/92 EB |

Primary Examiner—Robert W. Michell
Assistant Examiner—Francis J. Jaworski
Attorney, Agent, or Firm—Ervin B. Steinberg; Philip J. Feig

[57] ABSTRACT

A pulse-echo ultrasonic transducer probe includes a substantially centrally disposed axial bore running therethrough and a radial slot extending from the bore to the periphery of its housing. A slotted cap dimensioned to rotatably fit over the top of the housing is provided with a hollow semi-circular stem extending into the bore, the slot of the cap being aligned with the longitudinal opening of the stem. The slot of the cap and that of the transducer, when passing a surgical instrument through the bore into an opaque body, are rotatably adjusted so that they are out of registry with one another for supporting the surgical instrument and for maintaining the instrument in the center of an ultrasonic search beam. Subsequently, after the instrument has reached the desired position in the body the slots are brought into registry for providing removal of the transducer probe from around the instrument.

10 Claims, 10 Drawing Figures

TIME (DISTANCE)

TRANSDUCER PROBE FOR PULSE-ECHO ULTRASONIC EXPLORATION

BRIEF SUMMARY OF THE INVENTION

This invention refers to a transducer probe for pulse-echo ultrasonic exploration and specifically to a transducer probe for use in medical or surgical procedures. More specifically, the present invention refers to an ultrasonic transducer which is extremely useful when used in conjunction with certain surgical procedures involving the withdrawal of fluid or removal of tissue from an opaque body whereby the instrument or needle used for such purpose can be located more precisely within the body, and the progress of the surgical procedure can be monitored with a high degree of accuracy and reliability. Quite specifically, the transducer probe disclosed hereafter is designed to fit around surgical instruments, such as a biopsy or aspiration needle, in order to aid in the placing of the tip of such an instrument within a living body and to be removed from around the instrument after the needle is disposed at its desired position.

In U.S. Pat. No. 3,721,227, issued to E. A. Larson et al, entitled "Transducer for Pulse-Echo Ultrasonic Exploration", dated Mar. 20, 1973, a transducer having a centrally disposed axial bore for guiding a needle into a body is described. Also, in German Patentschrift 19 27 868, an annular transducer for locating a blood vessel and injecting a substance into the blood vessel is described. While the described annular transducer probe construction has met with great success, there appeared in connection with certain procedures a need for a transducer probe construction which provides for the removal of the transducer probe from around the needle after the needle is located at the desired position ready for fluid extraction or tissue removal. In response to this need, transducer probes were designed having a radial slot for permitting the removal of the probe from the needle.

Again, while meeting with great success it became apparent that the addition of a slot, while solving the removal problem, caused other problems concerning steadying the needle while it progressed into the body and maintaining the tip of the needle in the center of the ultrasonic beam. Since a portion of the transducer probe housing was left open, the needle could slip and undergo gross motion as the physician urged the needle into the body while simultaneously observing a CRT display to monitor the progress of the needle.

An object of the present invention is the provision of a transducer probe which overcomes the limitations found in the prior constructions. The construction disclosed hereafter provides for support of the needle while it is urged into the body and for the operator to remove the transducer probe from the needle after the needle is in its proper position. To this end, a cap having a stem and slot registration means is provided for use with a conventional radially slotted transducer probe to enable the operator to selectively place the slot of the cap and the slot of the housing into or out of registration for capturing and releasing the needle. The cap and stem preferably are contructed of stainless steel to facilitate sterilization by autoclaving.

Further and other objects of this invention will become more clearly apparent when the following specification is read in conjunction with the accompanying drawings.

DETAILED DESCRIPTION OF THE INVENTION

Figure 1:
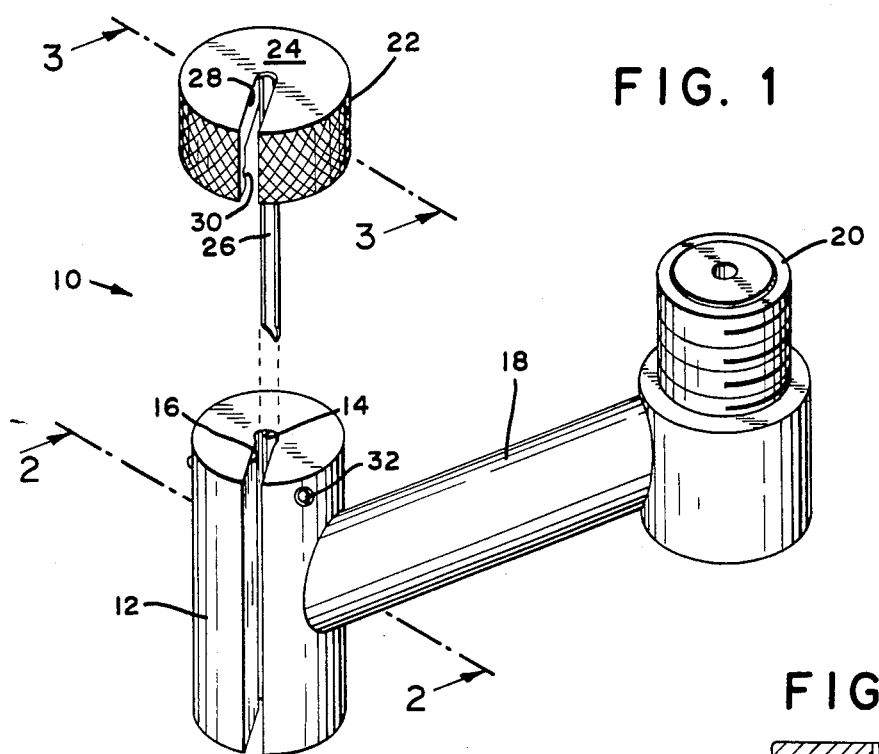
FIG. 1 is a perspective view of the transducer probe construction comprising the present invention.

Referring now to the figures and FIG. 1 in particular there is shown a transducer probe 10 comprising a generally cylindrical housing 12 having an axially disposed bore 14 and a radial slot 16 extending along the length of the housing from the bore 14 to the periphery of the housing 12. Extending from the housing 12 is an arm 18 for manipulating the transducer 10. The distal end of the arm 18 is terminated in a connector 20 for providing electrical connection to a pulse-echo ultrasonic diagnostic instrument, the construction of which is known in the art. The transducer probe housing construction is known in the art and is generally referred to as a notched aspiration/biopsy transducer probe.

Figure 3:
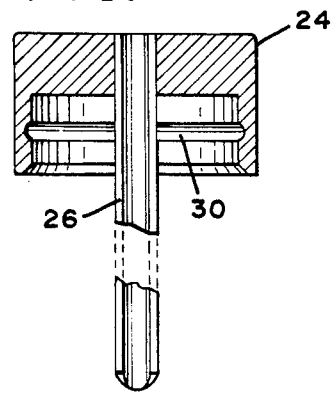
FIG. 3 is a sectional view along the line 3—3 of another portion of the transducer probe shown in FIG. 1.
Figure 4A:
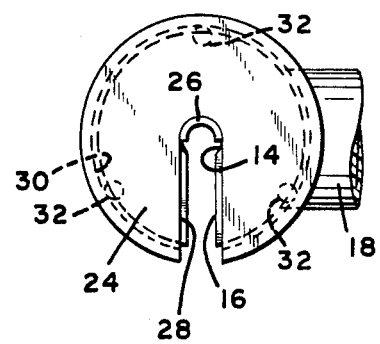
FIG. 4a is a plan view of the transducer probe shown in FIG. 1.

The transducer probe 10 further includes a cap and stem 22 comprising a generally hollow cylindrical slotted cap portion 24 and a depending stem 26 of semi-circular cross section generally dimensioned to fit within the bore 14 in housing 12. The diameter of the cap portion 24 is dimensioned such that when the stem 26 is disposed in bore 14, a groove 30 (see FIG. 3) machined in the inner wall of the hollow cap 24 engages a plurality of spring loaded pins 32 extending radially from housing 12 thereby providing for free rotation of the cap 22 and stem 26 with reference to the housing 12 while preventing motion of the cap and stem in a direction parallel to the longitudinal axis of the housing 12. In addition, the cap 24 has a centrally disposed bore and a radial slot 28 extending from the bore to the periphery of the cap, the slot 28 being aligned with the longitudinal opening of stem 26 for permitting, when the slot 28 and slot 16 are in registration (FIG. 4a), the transducer probe to be withdrawn in a lateral direction from around an instrument disposed in bore 14. The cap 24 and stem 26 are constructed of a material capable of being sterilized by autoclaving as required by surgical procedures, for instance, stainless steel.

Figure 2:
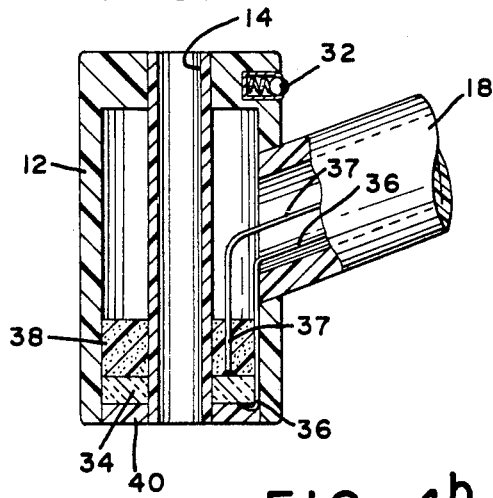
FIG. 2 is a sectional view along the line 2—2 of a portion of the transducer probe shown in FIG. 1.

The construction of the transducer probe 10 as best seen in FIG. 2 includes a piezoelectric wafer 34, typically made of lead zirconate titanate, whose opposite radial surfaces are connected to a pair of electrical conductors 36 and 37 as is well known in the art. The rear surface of the wafer 34 is in contact with a damping material 38, for instance a tungsten powder filled plastic resin material. The front surface of the piezoelectric material is covered by an acoustic matching and protective plate 40 made, for instance, of epoxy material. The elements described are enclosed within the housing 12 which completely insulates the encapsulated structure to withstand a breakdown voltage of at least 2,500 volts alternating current between any surfaces. The housing also is constructed of a material which is suitable for sterilization by gas sterilization as required for surgical procedures.

Figure 5A:
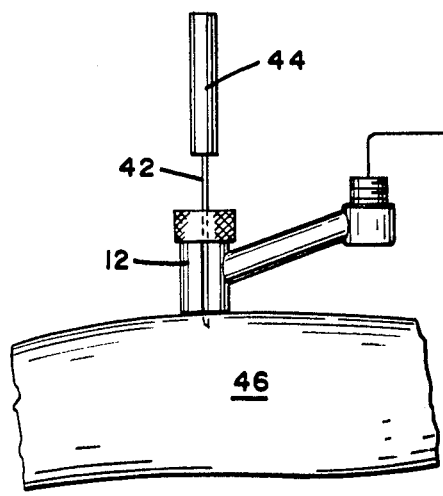
FIGS 5a and 5b are illustrations of the use of the transducer probe in conjunction with a surgical instrument or other medical device.
Figure 5B:
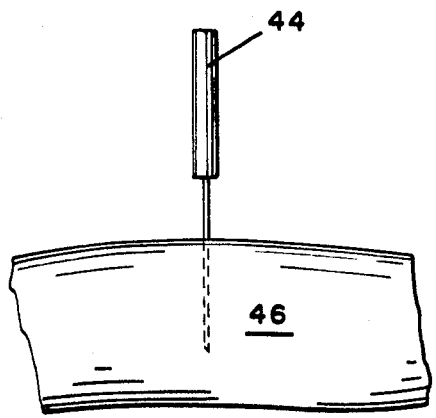

The wafer 34 is dimensioned to conform generally to the cross section of the housing 12, i.e. the wafer 34 has a centrally disposed axial bore and slot aligned with the slot of the housing 12. The diameter of the centrally disposed bore 14 in housing 12 is selected so that the transducer probe 10 slidingly fits over a surgical instrument, such as needle 42 of an aspiration device 44 (FIG. 5a). In a typical example the inside diameter of the bore 14 has a diameter of approximately 2.6 to 2.7 mm which allows most common aspiration and biopsy needles to be passed through the transducer probe center and also allows sufficient room for a sterile tubing (not shown) to be inserted into the bore 14 to prevent contamination of the sterile needle 42 when it is passed through.

If the surgical instrument has a rectangular cross section, the bore 14 and the bore in the cap 24 will be made to provide a corresponding cross section. Alternatively, liners may be used to provide the appropriate clearance and fit.

Figure 4B:
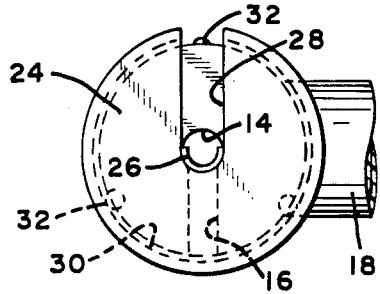
FIG. 4b is a view similar to FIG. 4a, except that the cap has been rotated by 180°.

The stem 26 is initially positioned in the bore 14 as shown in FIG. 4b, the notches 16 and 28 are out of registration and bore 14 and stem 26 form a closed cylindrical bore. As shown in FIG. 5a, the transducer probe 10 is disposed on the body 46 in the region where the surgical procedure is to be performed. A thin film of sterile couplant material is interposed between the transducer probe 10 and the body 46. Assuming that the surgical instrument is an aspiration device 44 and the needle 42 is to be inserted into a cyst for the purpose of draining fluid from the cyst, the radially closed bore provides support and steadies the needle 42 as it is urged toward the cyst, retaining the tip of the needle in the center of the ultrasonic search beam.

Figure 6A:
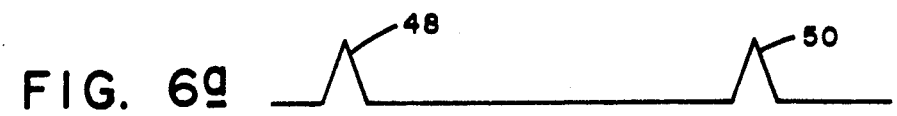
FIGS. 6a, 6b and 6c are graphical representations of the display obtained on a cathode ray oscilloscope when using the transducer probe in combination with a surgical instrument.

The transducer probe 10 is connected via connector 20 to a standard pulse-echo instrument having a cathode ray tube screen. The progress of the procedure is clearly visible by reference to FIG. 6a which indicates the signals on a cathode ray tube using a conventional A-scan. When the transducer probe is energized with electrical energy, an ultrasonic search signal is transmitted toward the interior of the body 46 and echo signals are received upon the search signal intercepting acoustic discontinuities, e.g. signal 48 represents the echo signal originating from the front surface of the cyst and signal 50 represents the echo signal originating from the rear surface of the cyst.

Figure 6B:
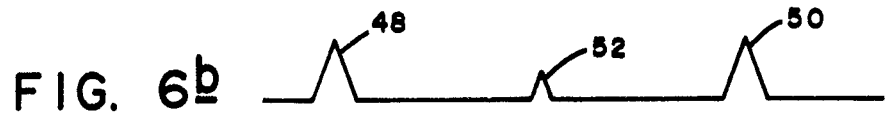
Figure 6C:
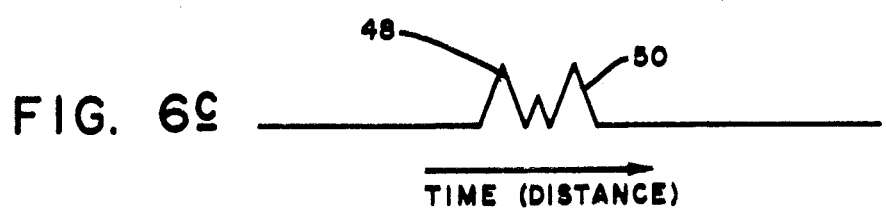

The needle 42 is advanced through the center of the closed bore until the screen shows the waveform per FIG. 6b when the tip of the needle 42, maintained in the center of the search beam, reflects an echo signal 52 disposed timewise between the echo signals 48 and 50. When the needle 42 is in the desired position, the cap 24 is rotated 180° for causing the slot 28 to be in registration with the slot 16 in housing 12 (FIG. 4a) thus permitting lateral removal of the transducer probe 10 from around the needle 42 during the ensuing aspiration procedure. Of course, the transducer probe 10 may be repositioned around the needle 42 at any time to monitor progress of the procedure. Responsive to aspiration, FIG. 6c, the cyst collapses as is clearly evident from the narrowed space between the signals 48 and 50 at which time the needle 42 is withdrawn from the body 46.

It will be apparent that the same procedure may be employed using a transducer probe comprising a housing 12 having a finger grip and a pair of conductors in lieu of an arm 18. It has been found useful to employ an arm 18 as shown for allowing the plate 40 to maintain contact with the body 46 when the arm 18 is resting on a higher area such as a rib. Moreover, the outer surface of cap 24 may be knurled to facilitate gripping for bringing the slot 28 into and out of registration. Typical frequency of the ultrasonic search signal is 2.25 Megahertz although other frequencies in the range between 0.5 and 10 Megahertz may be used to suit a particular procedure.

It will also be apparent that the transducer probe may be constructed using a cap without a stem. The closure formed by the cap and the housing provides the necessary support for the instrument.

It will also be understood that the instant transducer probe is extremely valuable in placing surgical instruments accurately within a living organism and monitoring the progress of the particular surgical procedure. Removal of the transducer during the aspiration procedure provides the further advantage of freeing the needle from any obstructions or the like.

While a preferred embodiment of a transducer probe has been described and illustrated, it will be apparent to those skilled in the art that further modifications and variations may be made without deviating from the broad scope of the invention which shall be limited solely by the appended claims.

What is claimed is:

1. A transducer probe for pulse-echo ultrasonic exploration of a biological body comprising in combination a housing, a piezoelectric wafer disposed in said housing and adapted to be acoustically coupled to said body, electrical connections coupled to said wafer for applying electrical pulse signals to said wafer and providing electrical signals responsive to acoustic echo signals received by said wafer, a backing layer contacting one side of said wafer for damping acoustic energy received by said wafer, a bore disposed substantially centrally through the thickness of said wafer and extending through said backing layer and housing, and a radial slot extending from said bore to the periphery of said housing wherein the improvement comprises:

cap means having a depending stem adapted to extend into said bore coupled to said housing for rotation with respect to said housing; said cap means and stem having aligned radial slots for providing when said cap means is rotated on said housing to cause the slot of said cap means and of said stem to be out of registry with respect to the slot in said housing a bore which encircles a surgical instrument inserted into the bore, and for providing when said respective slots are in registry a radial slot for removing said transducer probe in a lateral direction from around said instrument.

2. A transducer probe as set forth in claim 1, said cap means and said housing including complementary engagement means which responsive to being interconnected provide rotational motion of said cap means relative to said housing but inhibit motion of said cap means along the longitudinal axis of said housing.

3. Transducer probe as set forth in claim 2, said complementary engaging means comprising a circular groove in one of said cap means or said housing dimensioned to engage at least one circumferentially disposed resiliently biased pin in the other of said cap means or housing.

4. A transducer probe as set forth in claim 1, and a protective plate disposed in front of said wafer for contacting the body to be explored.

5. A transducer probe as set forth in claim 1, and an arm extended from the periphery of said housing at a location other than at said radial slot having its end adapted to be coupled to a nondestructive testing device.

6. A transducer probe for pulse-echo ultrasonic exploration comprising:
- a housing having a substantially centrally disposed axial bore therethrough and a slot extending from said bore to the periphery of said housing;
- a piezoelectric element disposed in said housing for transmitting responsive to being energized, an ultrasonic search signal into a body and receiving echo signals therefrom; and
- a cap adapted to be coupled to said housing and having a substantially centrally disposed bore therethrough and a slot extending from said bore to the periphery of said housing, said cap means being rotatable on said housing for causing said slot in said cap to be selectively in and out of registration with said slot in said housing.

7. A transducer probe as set forth in claim 6, said cap including a stem extending from the periphery of said bore in said cap at a region substantially opposite said slot in said cap and said stem being dimensioned for insertion into said bore of said housing.

8. A transducer probe as set forth in claim 7, said stem being hollow and of substantially semi-circular cross-section for conforming to the contour of said axial bore in said housing when said slots are in registration.

9. A transducer probe as set forth in claim 6, said cap and said housing including complementary engagement means which responsive to being interconnected provide rotational motion of said cap relative to said housing but inhibit motion of said cap along the longitudinal axis of said housing.

10. A transducer probe as set forth in claim 9, said complementary engagement means comprising a radially disposed resiliently biased pin in one of said cap or said housing and a groove in the other of said cap or said housing.

* * * * *